US00PP21513P3

(12) United States Plant Patent
Fotinos

(10) Patent No.: US PP21,513 P3
(45) Date of Patent: Nov. 23, 2010

(54) ***HYDRANGEA* PLANT NAMED 'HYDFOUR'**
(50) Latin Name: *Hydrangea macrophylla*
Varietal Denomination: HYDfour

(76) Inventor: Peter Fotinos, 905 S. Patterson Ave., Santa Barbara, CA (US) 93111

( * ) Notice: Subject to any disclaimer, the term of this patent is extended or adjusted under 35 U.S.C. 154(b) by 157 days.
(21) Appl. No.: 12/315,939
(22) Filed: Dec. 9, 2008
(65) Prior Publication Data
US 2010/0146674 P1 Jun. 10, 2010
(51) Int. Cl.
*A01H 5/00* (2006.01)
(52) U.S. Cl. ..... Plt./250
(58) Field of Classification Search ..... Plt./250
See application file for complete search history.
*Primary Examiner*—Susan B McCormick Ewoldt

(57) ABSTRACT

A new *Hydrangea* plant, which has abundant, pink colored double flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

4 Drawing Sheets

Latin name of genus and species: *Hydrangea macrophylla* 'HYDfour'.

Variety denomination: The new variety is named 'HYDfour'.

BACKGROUND OF THE INVENTION

The present invention constitutes a new and distinct variety of *Hydrangea* plant, which was developed by artificially pollinating an unnamed seedling(not patent in the US) with an unnamed seedling (not patent in the US). The two parents were crossed in the spring of 2005 and the resulting seed was sown in September 2005, in a controlled glasshouse environment. Out of these seedlings one seedling was selected, as the new variety and named 'HYDfour'. The new *Hydrangea* plant may be distinguished from its seed parent, an unnamed seedling, by the following combination of characteristics:

1. The unnamed seedling has a breeding background in unnamed seedlings.
2. 'HYDfour' has medium dome-shaped inflorescences, while the unnamed seedling has large dome-shaped inflorescences.
3. 'HYDfour' has pink colored flowers, while the unnamed seedling has red flowers.

The new variety may distinguished from its pollen parent, an unnamed seedling created by the same inventor, by the following combination of characteristics:

1. The unnamed seedling has a breeding background in unnamed seedlings.
2. 'HYDfour' has medium dome-shaped inflorescences, while the unnamed seedling has small flat inflorescences. 'HYDfour' has pink flowers, while the unnamed seedling has red flowers.

BRIEF SUMMARY OF THE INVENTION

Initial asexual reproduction of 'HYDfour' by cuttings was first done in Santa Barbara, Calif., USA. The reproduction was conducted in controlled greenhouse environments.

Have here proven that the foregoing and all after characteristics and distinctions to come true to form and are established in succeeding propagations. 'HYDfour' is a low and compact *Hydrangea* plant with good vigor. The objective of the hybridization of this *Hydrangea* variety for commercial greenhouse culture was to create a new and distinct variety with:

1. Uniform and abundant flowers with good keepability;
2. Attractive long lasting foliage and compact growth,
3. Year round flowering under glasshouse conditions;
4. Suitability for production from softwood cuttings in pots.;
5. Durable flowers and foliage which make the variety suitable for distribution in the floral industry.

This combination of qualities was not present in previously available commercial cultivars of this type and distinguish 'HYDfour' from all other varieties of which we are aware.

The seeds, from hybridization were planted in a controlled environment and evaluations were conducted on the resulting plants. 'HYDfour' was selected by Peter Fotinos, in his development program in Santa Barbara, Calif., USA.

BRIEF DESCRIPTION OF THE DRAWINGS

The accompanying color illustrations show as true as is reasonably to obtain in color photographs of this type, the typical characteristics of the buds, flowers, leaves, stems of 'HYDfour'. Specifically illustrated in the drawings:

On sheet 1/4:
FIG. 8: Corymb unfolded stages.
On sheet 4/4.

DETAILED BOTANICAL DESCRIPTION OF THE VARIETY

Figures 1, 2, 3, 4, 5:
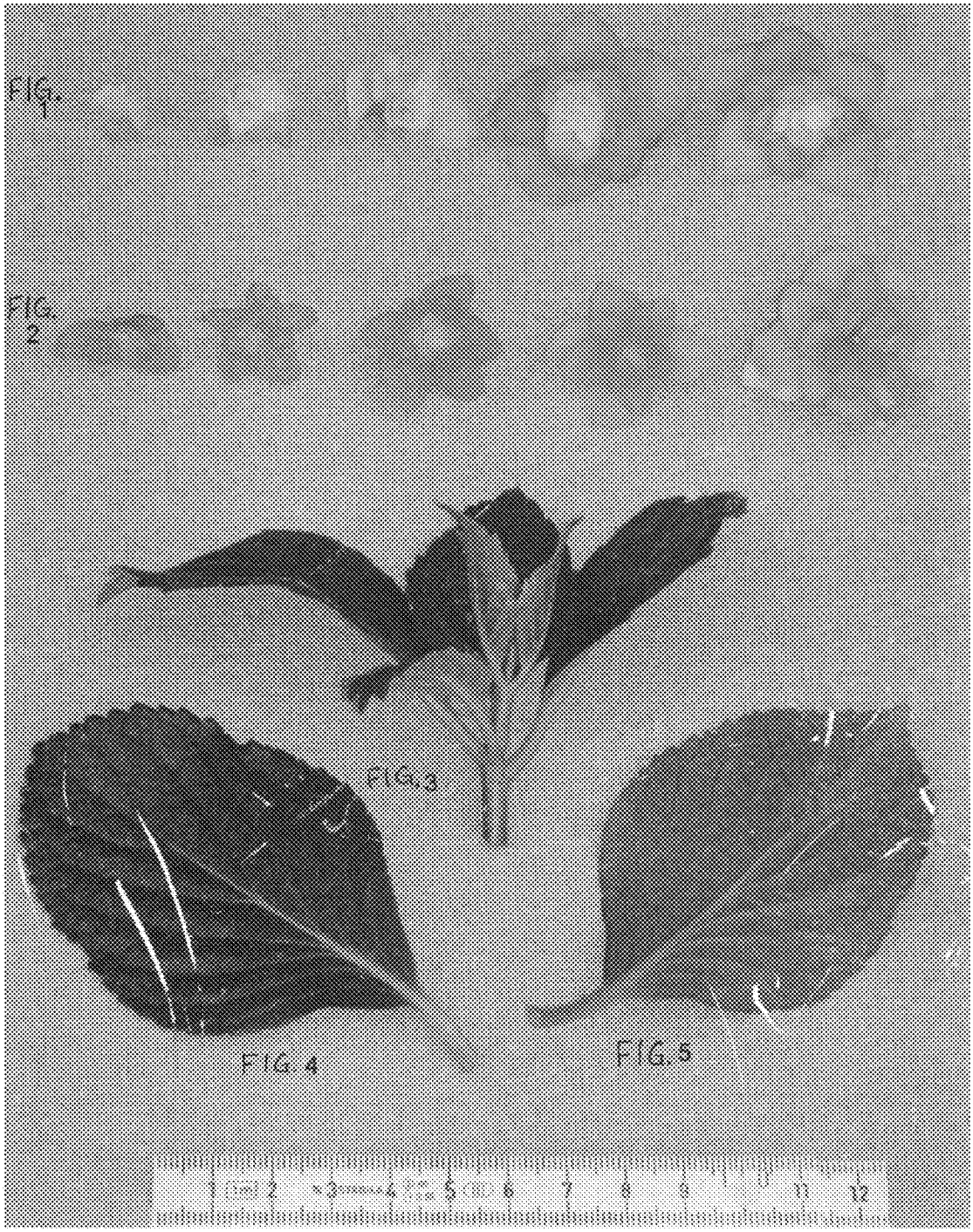
FIG. 1: Development of Pink flowers.
FIG. 2: Developments of blue flowers.
FIG. 3: Tip of young shoot.
FIG. 4: Mature leaf, upper side.
FIG. 5: Mature leaf, reverse side.
On sheet 2/4.
Figures 6, 7:
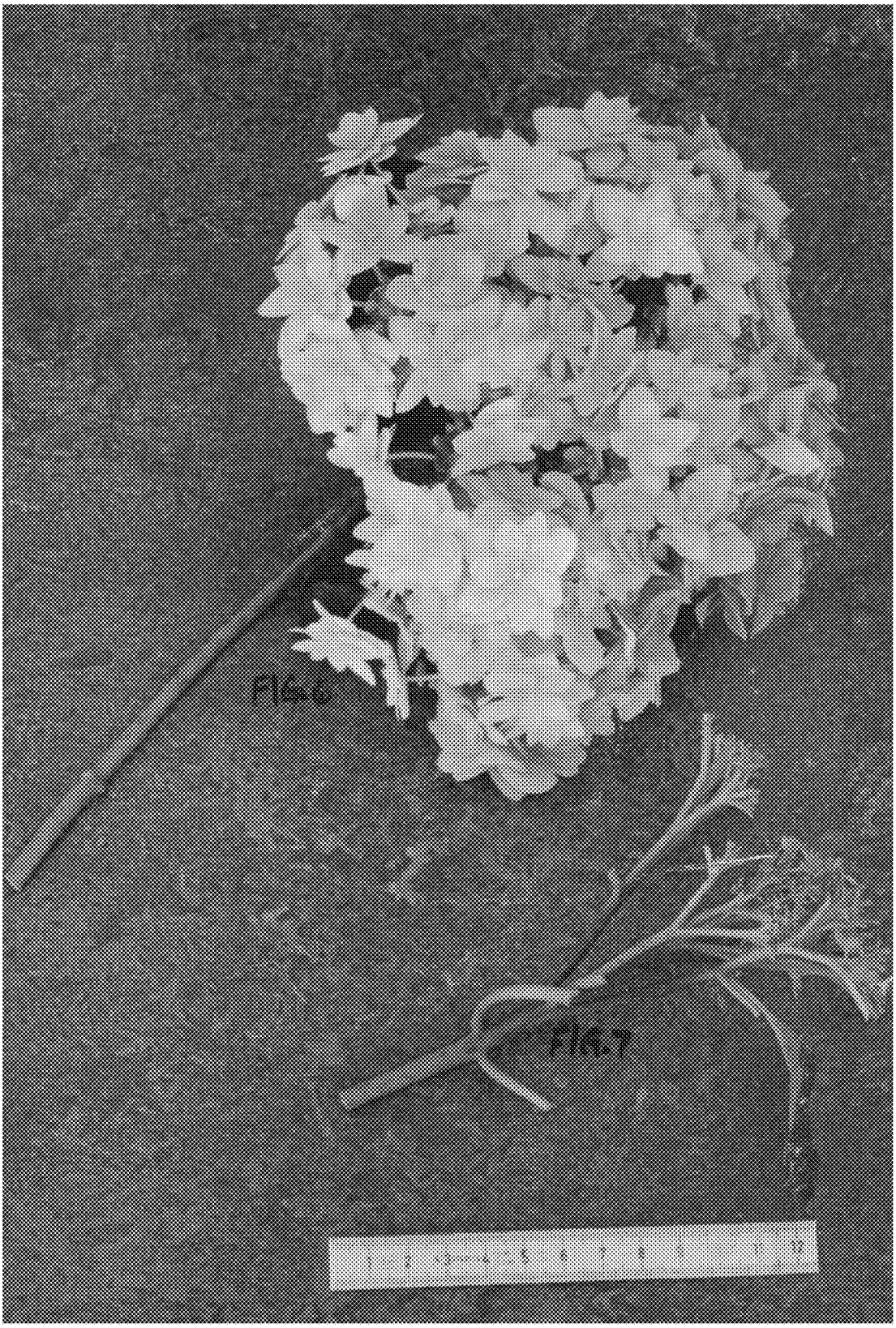
FIG. 6: Bare stem with flower head starting to unfold.
FIG. 7: Corymb with flowers detached.
On sheet 3/4.
Figure 3:
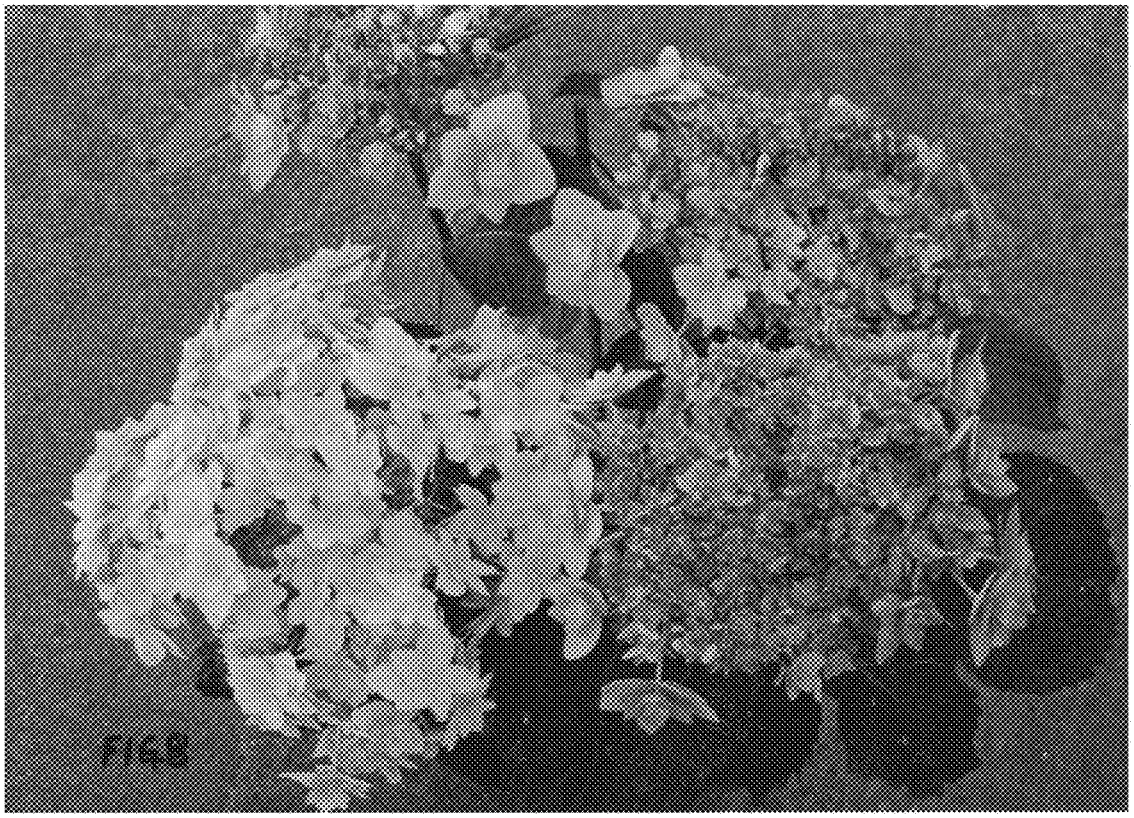
Figure 9:
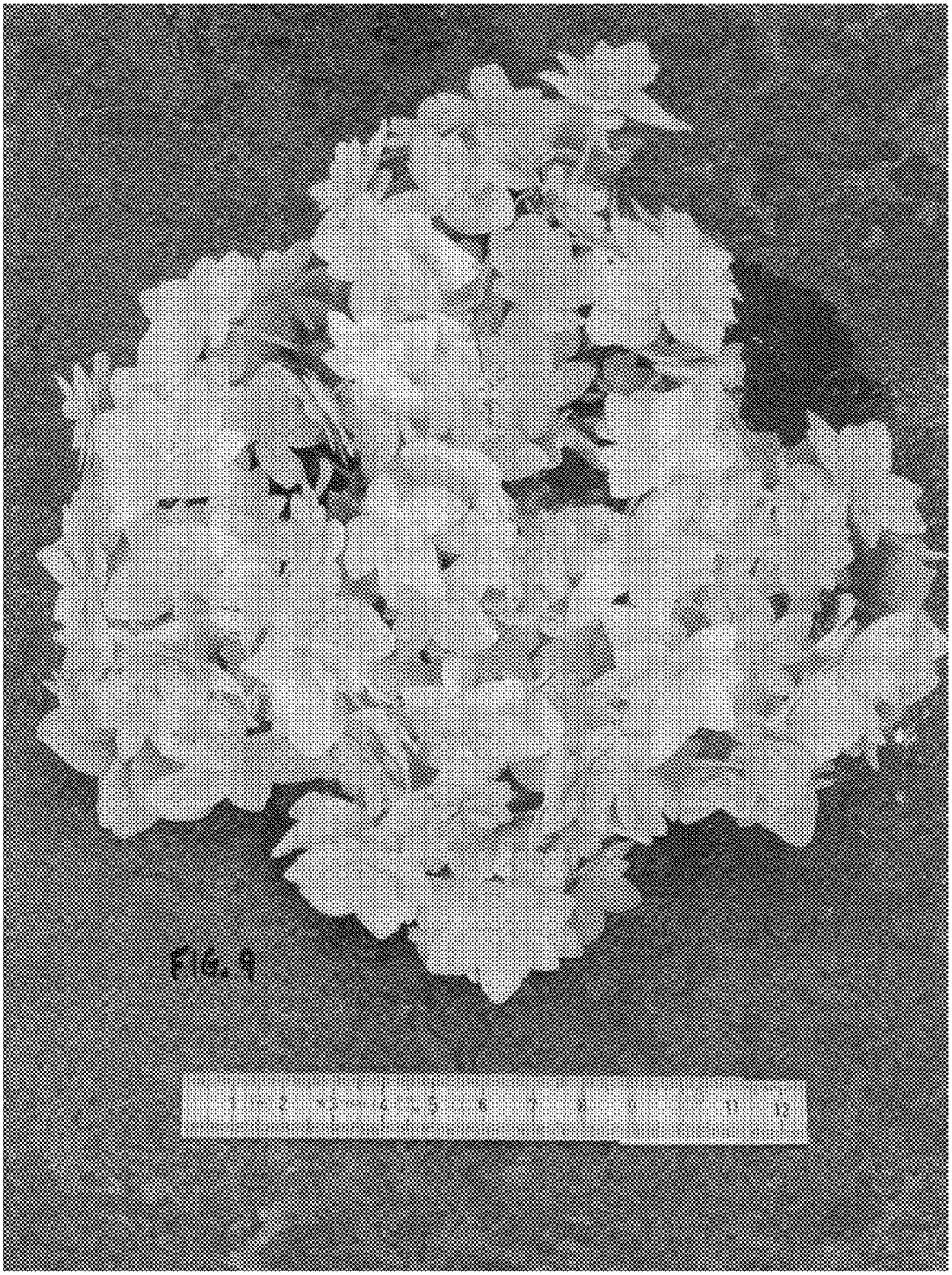
FIG. 9: Corymb fully unfolded pink.

The following is a detailed description of the *Hydrangea* plant: *Hydrangea macrophylla* 'HYDfour'.

The following observations, measurements, values and comparisons describe plants grown in glass houses in Santa Barbara, Calif., USA.

The age of the observed plants where 29 to 33 weeks after propagation by cuttings, and produced as flowering pot plants in container of 16 centimeter in diameter.

Environmental conditions in the cultivation area for the observed plants, has been temperatures from 36 to 78 degree Farenheit, and 10 to 20 hours day length with assimilation light. Light levels from 600 foot candle to 6000 foot candle. The relative humidity has been ranging from 50 to 85%.

Color references are made using The Royal Horticultural Society (London, England) Colour Chart, 1995, except where common terms of color are used. For a comparison, the nearest existing *Hydrangea* variety is 'RIE 05', a *Hydrangea* variety described and illustrated in U.S. Plant Pat. No. 18,508. Chart 1 details several physical characteristics of 'HYDfour' and 'RIE 05'.

CHART 1

| | 'HYDfour' | 'RIE 05' |
|---|---|---|
| Sepal color, Upper surface | Red-Purple Group 73B to 73D | Red-Purple Group 62C And 62D |
| Sepal color, Reverse surface | Red-Purple Group 73B to 73D | Purple Group 75B, And veins 75A |
| Petal count | 15 to 25 | 12 average |

*Parents.*—Unnamed seedling×unnamed seedling.

Classification:

*Botanical.*—*Hydrangea macrophylla.*

*Commercial.*—Pot *Hydrangea.*

Plant:

*Plant growth.*—Moderately vigorous. Grows compact upright to bushy. When grown as 11 cm pot plant, the average height of the plant itself is 20 to 22 cm, and average width is 21 cm. When grown as a 16 cm pot plant, the average height of the plant itself is 24 to 36 cm, and average width is 30 cm. The plant form is rounded. Production time is generally 29 to 33 weeks depending on average temperature, light level, and cultural practices. To create pink flower heads the plants was grown at pH 6.0. To create blue flower heads the plants was grown at pH 4.5 and Aluminum at 20 ppm was added to the irrigation water.

Stem:

*Color.*—Young wood: Green Group 141C, with intonations of Greyed-Purple Group 187C, at the internode base. Older wood: Green Group 141B.

*Lenticels.*—Incidence: 120 to 140 per internode. Size: 0.3 to 0.5 mm. Color: Greyed-Purple Group 187C. Shape: Round to ovate.

*Surface.*—Young wood: Smooth. Older wood: Smooth.

*Stem diameter.*—4 to 5 mm.

*Internode length.*—20 to 40 mm.

*Numbers of internodes.*—3 to 4.

Plant foliage: Leaves arranged alternately, generally symmetrical, abundant, and flat in aspect. The venation pattern is pinnate.

*Quantity of leaves.*—6 to 8 per lateral branch(stem).

*Petioles.*—Color: Green Group 141D, Margins: Entire. Length: 12 to 18 mm. Diameter: about 3 to 4 mm.

*Leaves.*—Edge: Serrated. Serration: Single. Shape: Ovate with acuminate apex and obtuse to acuminate base. Texture: Coriaceous. Appearance: Dull. Size: Length: 60 to 90 mm. Width: 35 to 55 mm. Color: Young foliage: Upper surface: Green Group 136B. Lower surface: Green Group 143C. Color: Mature foliage: Upper surface: Yellow-Green Group 136A. Lower surface: Green Group 137C. Leaf vein color: Upper surface: Yellow-Green Group 136B. Reverse surface: Yellow-Green Group 137D.

Inflorescense:

*Blooming habit.*—Seasonal, natural flowering in spring-summer season.

*Fragance.*—None.

*Flower type.*—Single flowers densely arranged on a corymb spherical formed head. Corymb size: 12 to 16 cm in diameter. Arrangement: Pedicels of the sterile flowers are longer than the pedicels of the fertile flowers so that the fertile flowers are below the sterile flowers in the flower head. Fertile Flowers: 80 to 100 per flower head, with 14 to 18 petals. Sterile flowers: 40 to 170 per flower head, with 20 to 24 sepals per flower.

*Flowerbuds.*—Length: 1 to 2 mm. Diameter: 1 to 2 mm. Shape: Ovoid. Color: Yellow-Green Group 145B.

*Peduncle.*—Color: Yellow-Green Group 141B, with intonations of Grey-Purple Group 187D. Texture: Smooth, with lenticels of Grey-Purple Group 187D. Length: 25 to 35 mm. Diameter: 2 to 3 mm. Strength: Erect, strong. Count: 3 to 4 per stem.

*Pedicel.*—Color: Greyed-White Group 157D, with intonations of Grey-Purple Group 186D, and for aluminum treatment also intonations of Violet-Blue Group 90D towards the end of the pedicel. Texture: Smooth. Length: 15 to 25 mm. Diameter: 1 to 2 mm. Count: 18 to 50 per peduncle. Strength: Erect, strong.

*Sterile flower.*—Form: Shape of flower when viewed from the side. Up on opening: Cupped. Open flower: Flat. Size: 10 to 35 mm in diameter. Sepals: 20 to 24 per sterile flower, Sepal size: Length: 5 to 15 mm. Width: 3 to 15 mm. Sepal shape: Orbicular with emarginated tip. Texture: Smooth. Margin: Single serrated. Appearance: Dull. Color: At emerging flower head Upper surface: At pH 6.0: White Group 155D, with intonations of Yellow-Green Group 144A. At pH 4.5: White Group 155D, with intonations of Yellow-Green Group 144A. Reverse surface: At pH 6.0: White Group 155D, with intonations of Yellow-GreenGroup 144A. At pH 4.5: White Group 155D, with intonations of Yellow-Green Group 144A. Full unfolded flower head. Upper surface: At pH 6.0: Red-Purple Group in the range from 73B to 73D, Intonations of Yellow-White Group 158C as center of each Sterile flower. At pH 4.5: Blue Group in the range from 105B to 106D. Intonations of Yellow-White Group 158C as the center of the sterile flowers. Reverse surface: At pH 6.0: Red-Purple Group in the range from 73B to 73D. At pH 4.5: Blue Group in the range from 105B to 106D. Intensity is increasing towards the veins. Eye: Color: Yellow-White Group 158C. Size: 0.5 to 2 mm in diameter.

*Fertile flower.*—Size: 3-5 mm in diameter. Form: Shape of flower when viewed from the side. Up on opening: Cupped. Open flower: Cupped. Color: Petals, upon opening. Upper surface: At pH 6.0: Yellow-Green Group 144A. At pH 4.5: Yellow-Green Group 144A. Reverse surface: At pH 6.0: Yellow-Green Group 144A. At pH 4.5: Yellow-Green Group 144A. Petals after opening: Outward surface: At pH 6.0: Red- Purple Group 73B. At pH 4.5: Blue Group 105B to 106D. Inward surface: At pH 6.0: Red-Purple Group 73B. At pH 4.5: Blue Group 105B to 106D.

*Petals.*—Petal reflex. Outermost petals reflex inwards at opening. Fully open all petals reflex inwards. Texture. Smooth. Petal edge. Entire. Petal count. 14 to 18 per flower. Petal size. Length 2-3 mm. Width: 1-2 mm. Shape. Round — ovate.

*Reproductive organs* (*Only present on fertile flowers*) .—Stamen number: 3 to 4 per flower. Anther shape: Two-lobed. Anther color: At pH 6.0: Red-Purple Group 73B. At pH 4.5: Blue Group 106B. Pollen amount: Scarce. Pollen color: White Group 155B. Filament: Color, White Group 155B. Length 1 mm. Pistils number: 3 to 4 per flower. Pistils: Stigma shape: Round. Stigma color: White Group 155A. Style: Color, White Group 155A. Length 1 mm.

Development:

*Vegetation.*—Dense.

*Blooming.*—Abundant.

*Aptitude to bear fruit.*—Poor.

*Resistance to diseases.*—Above average resistance to mildew and Botrytis under normal growing conditions in Santa Barbara, Calif.

*Seeds has not been observed.*—Due to that the plant has never been grown to the stage of seed development, due to the fact, that the variety is developed for use as a flowering pot plant only.

*Winter hardiness & Drought/heat tolerance.*—Due to the fact, that this variety is a potted flowering plant, developed indoor use only, the plant are not tested for winter hardiness or drought/heat tolerance.

The invention claimed is:

1. A new and distinct variety of *Hydrangea* plant, substantially as herein illustrated and described as a distinct and novel *Hydrangea* variety due to its abundant pink double flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *